United States Patent [19]

Bowen

[11] Patent Number: 5,053,197

[45] Date of Patent: Oct. 1, 1991

[54] DIAGNOSTIC ASSAY MODULE

[75] Inventor: Mark S. Bowen, Medford, Mass.

[73] Assignee: PB Diagnostic Systems, Inc., Westwood, Mass.

[21] Appl. No.: 382,552

[22] Filed: Jul. 19, 1989

[51] Int. Cl.$^5$ ............................................ G01N 33/00
[52] U.S. Cl. ...................................... 422/58; 422/56; 422/57; 422/82.05; 422/82.09; 422/61; 436/805; 436/169
[58] Field of Search .................. 422/57, 56, 58, 82.05, 422/82.09, 61; 436/805, 169

[56] References Cited

U.S. PATENT DOCUMENTS

| | | | |
|---|---|---|---|
| 4,233,029 | 11/1980 | Columbus | 422/58 |
| 4,387,990 | 6/1983 | Yazawa et al. | 356/244 |
| 4,440,301 | 4/1984 | Intengan | 206/456 |
| 4,549,655 | 10/1985 | Forsythe, Jr. et al. | 206/569 |
| 4,668,472 | 5/1987 | Sakamoto et al. | 422/56 |
| 4,719,085 | 1/1988 | Jacobs | 422/56 |
| 4,789,628 | 12/1988 | Nayak | 422/58 X |
| 4,818,677 | 4/1989 | Hay-Kaufman et al. | 422/56 X |
| 4,906,439 | 3/1990 | Grenner | 422/56 |
| 4,912,034 | 3/1990 | Kalra et al. | 422/56 X |
| 4,943,522 | 7/1990 | Eisinger et al. | 422/57 X |

FOREIGN PATENT DOCUMENTS 0215419 3/1987 European Pat. Off. .
0306336 3/1989 European Pat. Off. .

Primary Examiner—Robert J. Warden
Assistant Examiner—Stephanie Blythe
Attorney, Agent, or Firm—Gaetano D. Maccarone

[57] ABSTRACT

A diagnostic assay module for analytical procedures in which an optical signal developed by interaction between a component in a sample fluid, such as an analyte in a biological fluid, and one or more reagents in a resilient assay element is read by optical means. The module includes a first member having one open side and a second member adapted to close the open side of the first member against a resilient assay element. The area of the assay element to which the sample fluid is applied and wherein the optical signal developed by the interaction of the sample component and the reagent(s) in the assay element is read is maintained in a substantially horizontal orientation by flexure developed between complementing ramp surfaces on the respective first and second members. In a preferred embodiment the first member defines a liquid transport surface which, together with the assay element forms a fluid flow zone to provide for the uniform spreading of a sample fluid, introduced through an aperture in the member, across the surface of the assay element. The volume of fluid in the fluid flow zone is controlled by the precise positioning of the assay element according to the invention.

17 Claims, 5 Drawing Sheets

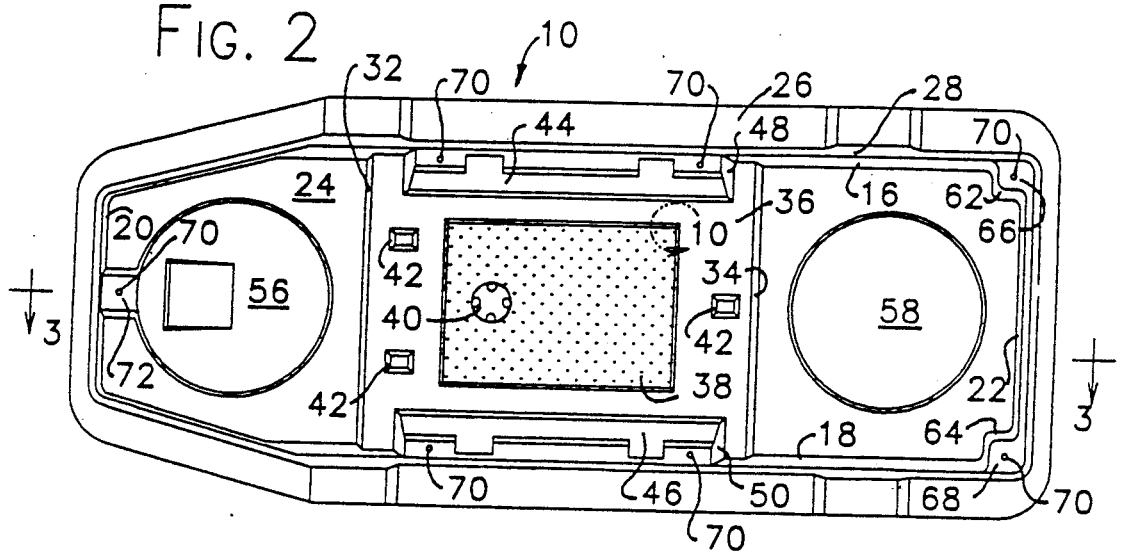
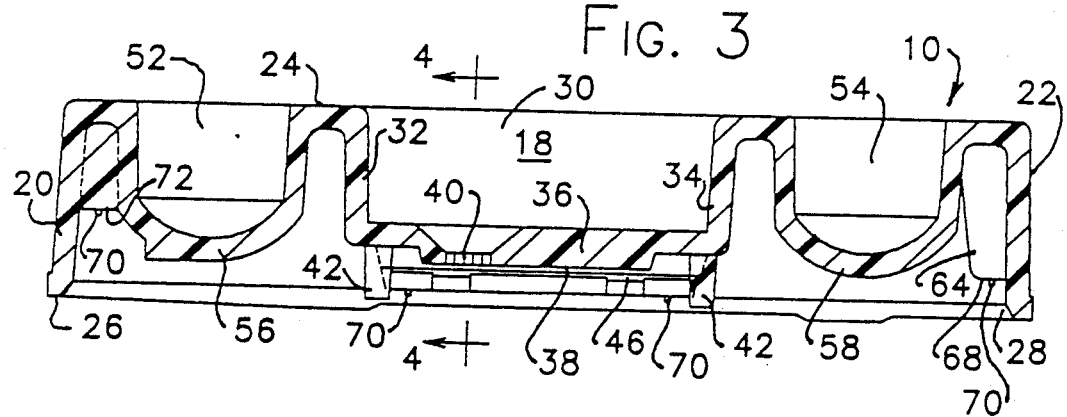
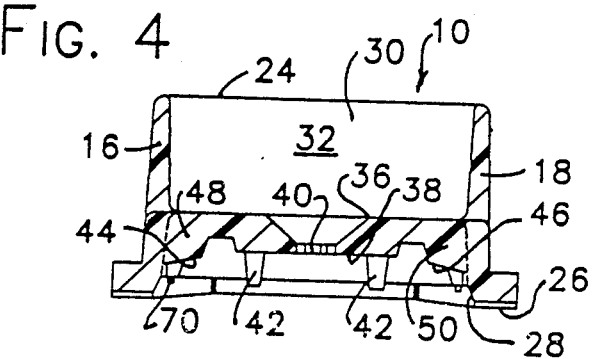

DIAGNOSTIC ASSAY MODULE

BACKGROUND OF THE INVENTION

This invention relates to diagnostic assay modules for analytical applications and, more particularly, it concerns assay modules including a resilient assay element wherein the interaction of a component in a sample fluid with one or more reagents present in the assay element causes a detectable change corresponding to the presence of the sample component.

In commonly assigned, copending U.S. patent application Ser. No. 210,732, filed June 23, 1988, entitled "LIQUID TRANSPORT SYSTEM", there is disclosed a liquid transport device which is particularly suited for use in immunoassay applications. In such applications a surface of an assay element is retained in contact or virtual contact with a relieved surface on the underside of a member which includes an aperture for allowing a sample fluid to be applied and distributed uniformly over the surface of the assay element. The relieved surface is defined by a plurality of projections arranged throughout the fluid flow zone to control the flow of fluid between opposed surfaces of the fluid flow zone. In a preferred embodiment the projections are arranged in orthogonal rows and columns to provide a uniform distribution of a sample fluid across the surface of an assay element. The positioning of the assay element in contact or virtual contact with the projections controls the volume of fluid in the fluid flow zone.

In addition to ensuring a uniform spread of the fluid sample across the surface of the assay element, the disclosure in this copending application recognizes the importance of retaining the assay element in a desired orientation to provide, among other purposes, for optical precision where the change resulting from interaction of a sample analyte with the assay element reagent(s) is read out by means of an optical apparatus. Retention of the assay element in such an orientation can be achieved by a support member arranged to engage the surface of the assay element in a manner to sandwich the element between a surface on the support member and the relieved surface. The support member is provided with a transparent window through which the change in the assay element may be read by the optical system. This arrangement is not completely satisfactory in all instances since the electromagnetic radiation used to read the change in the assay element must pass through the material from which the support member is made. Where relatively small changes are being read it may be more desirable not to interpose anything between the assay element and the optical system.

In another commonly assigned, copending U.S. patent application Ser. No. 378,647 filed July 12, 1989, entitled, "OPTICAL READ SYSTEM AND IMMUNOASSAY METHOD" now U.S. Pat. No. 4,977,325, a highly efficient dual channel fluorometer is disclosed in which enhanced optical efficiency enables the use of a low cost tungsten halogen illumination source in combination with solid state photodetectors to detect the low levels of sample emitted light encountered in fluoroanalysis. The optical system is embodied in an optics head designed to be positioned under a sample receiving vessel of the general type represented by the physical embodiment disclosed in the aforementioned copending application Ser. No. 210,732.

It is apparent from the combined disclosures of the aforementioned patent applications that the attainment of reliable results in analytical procedures requires the assay module in which the assay element is contained to accommodate the requirements for obtaining a uniform spread of the sample fluid across the surface of the assay element, for volume control of the fluid in a fluid flow zone where applicable and retention of the assay element under conditions which optimize the optical system by which the optical signal is read from the assay element. In this context, inclusion of a transparent window in the path of light directed to and reflected from the surface of the assay element represents an efficiency loss in the optical system of a magnitude which may have a substantial effect on the accuracy of the overall diagnostic equipment.

SUMMARY OF THE PRESENT INVENTION

In accordance with the present invention, there is provided an assay module which has a structure adapted for manufacture on a volume production basis and by which the very stringent tolerance requirements for retention and optical presentation of the assay element in the conduct of analytical procedures are achieved. Generally, the module includes two complementing molded parts which, when assembled with the assay element, retain the area of the assay element to which the sample fluid is applied and wherein the optical signal developed by the interaction of a sample component and the reagent(s) in the assay element is read in a substantially horizontal orientation by flexure developed between complementing ramp surfaces on the respective parts. In this manner the assay element can be optically located for reading by an optical system through an unobstructed opening in the assay module thereby obviating the need to interpose a support layer between the optical system and the assay element.

In a preferred embodiment of the invention, one of the members which form the assay module also defines a fluid transport surface which, together with the upper surface of the assay element defines a fluid transport zone to provide for the uniform spreading of a sample fluid across the surface of the element. The spreading of the sample fluid is achieved by a plurality of projections arranged throughout the intended fluid flow zone. As will be discussed in detail hereinafter in conjunction with the detailed description of the preferred embodiments of the invention, it is very important to control the volume of fluid which is present in the fluid flow zone above the assay element. In this embodiment of the invention the assay element is retained in contact or virtual contact with the plurality of projections which control the fluid flow thus providing precise control of the volume of fluid above the assay element as well as optically locating the assay element.

The two complementing members, which together with the assay element comprise the assay module of the invention, may be of various dimensions and may be provided initially as two separate parts or they may be joined such as by being hinged together so as to allow the assay module to be assembled after the assay element is inserted in place.

In a preferred embodiment, one of the molded parts of the assay module, hereinafter referred to the first, or top, member is of an oblong configuration and has one open side defined by a continuous peripheral lip on mutually opposed side and end walls which, in turn, join commonly with a closing wall. The closing wall is provided on its interior with a planar fluid transport surface of rectangular configuration and displaced toward the open side of the member from the remainder of the closure wall. A pair of inclined ramp formations in the side walls extend in parallel spaced relation from the side edges of the fluid transport zone and lie closer to the open side of the member than the fluid transport zone. The other of the two molded parts, hereinafter referred to as the second, or bottom, member is generally shaped as a plate member having a peripheral configuration to fit the open side of the first member. The second member is formed along opposite sides of its inner surface with ramp formations which complement the ramp surfaces on the side walls of the first member. A relatively large rectangular opening is provided between the ramp formations on the second member.

During assembly of the assay module, the assay element is positioned so that the side edges of the assay element overlie the respective ramp formations on the first and second members. When the two parts are closed against the assay element, the latter is flexed in a manner to be biased under the resiliency of the element into contact or virtual contact with the projections of the fluid transport surface and across the entire area of the intended fluid flow zone. The first and second members are then secured such as by adhesives, ultrasonic welding or the like.

The exterior of the top member of the assay module is shaped to define a relatively deep central well having a floor through which an aperture passes and opens to the fluid transport surface which carries the projections. The provision of the relatively deep well facilitates the introduction of sample fluid to the surface of the assay element at this time being flexed against the fluid transport surface. In addition, a pair of relatively deep cylindrical wells are provided in the exterior of the top member on opposite sides of the central well so that other fluids may be stored therein if desired.

A principal object of the invention is, therefore, the provision of an improved assay module for analytical applications. Another object is the provision of such a module in a structure capable of volume production while maintaining very close tolerances of the type required in immunoassay procedures. A still further object of the invention is to provide an assay module which facilitates the introduction of sample fluid to the surface of the assay element. Other objects and further scope of applicability of the present invention will become apparent from the detailed description to follow taken in conjunction with the accompanying drawings in which like parts are designated by like reference numerals.

BRIEF DESCRIPTION OF THE DRAWINGS

FIG. 2 is a bottom plan view of one of the parts shown in FIG. 1;

FIG. 3 is a cross section on line 3—3 of FIG. 2;

FIG. 4 is a cross section on line 4—4 of FIG. 3;

DETAILED DESCRIPTION OF THE PREFERRED EMBODIMENTS

Figure 1:
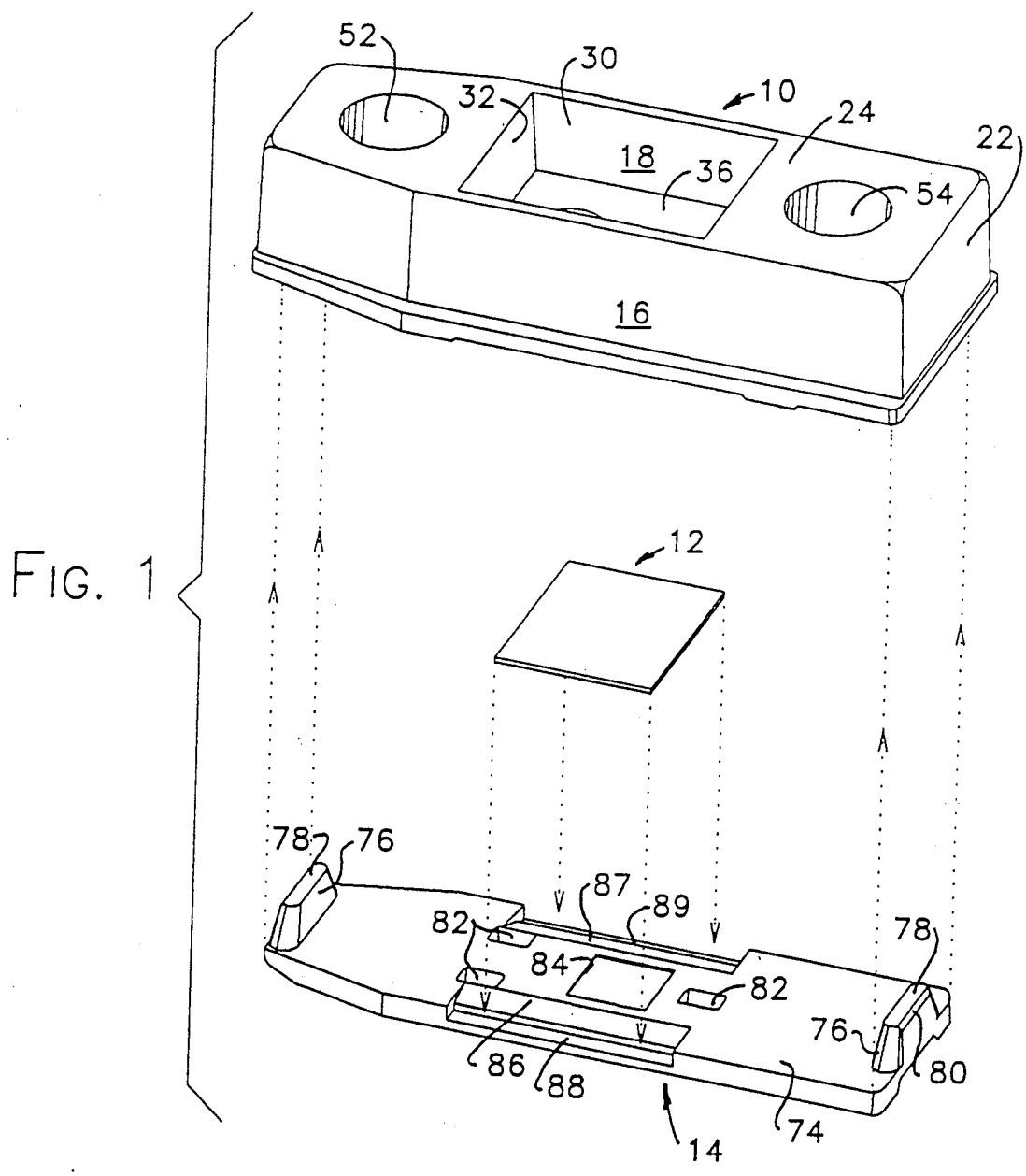
FIG. 1 is a exploded perspective view illustrating the respective parts of a preferred assay module according to the invention.

In FIG. 1 of the drawings, the principal parts of the assay module of the present invention are shown generally and prior to assembly as including a first, or top member 10, an assay element 12 and a second, or bottom, member 14. Although each of the parts 10, 12 and 14 will be described in considerably more detail below with reference to drawing figures illustrating such detail, it may be appreciated from FIG. 1 that the first member 10 and second member 14 are self-contained units capable of formation by injection molding techniques and may be closed one against the other to retain the assay element 12 in a precisely positioned location. Although the first member 10 has considerably higher sidewalls than the second member 14 in this preferred embodiment, the first and second members may be provided with various sidewall dimensions. For example, the first member may have relatively small sidewalls, particularly where fluid storage wells are not required. Further, although the first and second members are shown as two separate parts, as noted previously, they may be connected such as by being hinged together along one of their peripheral dimensions thus permitting them to be folded together and secured after the assay element is arranged in place.

In FIGS. 2-4 of the drawings, structural features of the first member 10 are detailed in bottom plan, longitudinal and transverse cross sectional views, respectively. In these figures it may be seen that the first member 10 is formed with mutually opposed side walls 16 and 18, end walls 20 and 22 and a shaped closure wall 24. The projecting edges of the side and end walls 16-22 define a peripheral flange-like lip 26 having a continuous chamfer 28 joining with the respective side and end walls.

In FIGS. 1, 3 and 4 of the drawings, it may be seen that the closure wall 24 is shaped to define with the side walls 16 and 18 a centrally located, generally rectangular well 30 delimited at opposite ends by mutually facing linear wall portions 32 and 34 extending between the side walls 16 and 18. The well 30 opens to the exterior of the first member 10 and is closed between the side walls 16 and 18 and wall portions 32 and 34 by a floor 36. Viewed from the opposite side of the well 30 or from the interior of the first member 10, the wall 36 is thickened centrally to establish a rectangular fluid transport surface 38 displaced from the interior surface of the wall 36 toward the open side of the first member circumscribed by the lip 26. A sample fill opening 40 opens through the floor 36 of the well 30 to the plane of the rectangular surface 38.

Also as may be seen in FIGS. 2-4, a plurality, specifically 3 post-like projections 42 extend from the inner surface of the well floor wall 36. The projections 42 are located to be spaced from the ends of the rectangular surface 38 and oriented such that one such post lies off one end of the rectangular surface 38 whereas the other two posts 42 lie off the opposite end of the rectangular surface 38. A pair of inclined ramp surfaces 44 and 46 are defined on step-like formations 48 and 50, respectively lying at the intersection of the inner surface of the ramp floor wall 36 and the interior of the side walls 16 and 18. As shown in FIG. 2, the ramp surfaces 44 and 46 are in spaced parallel relation with the side edges of the rectangular surface 38 and extend symmetrically beyond opposite ends of the surface 38. As may be seen most clearly in FIG. 4, the ramp surfaces 44 and 46 are displaced generally toward the lip 26 from the rectangular surface 38 and are inclined so as to diverge outwardly from the plane of the surface 38.

With reference to FIGS. 1 and 3, the first member 10 is formed with a pair of cylindrical wells 52 and 54 spaced from opposite ends of the central rectangular well 30. These cylindrical wells open through the outer surface of the covering wall 24 and are closed at their inner ends by dome-like formations 56 and 58, respectively. The cylindrical wells 52 and 54 may be used in practice to store other fluids such as diluents or reagents used in the analytical procedures in which the assay module of the invention is used.

Figure 11:
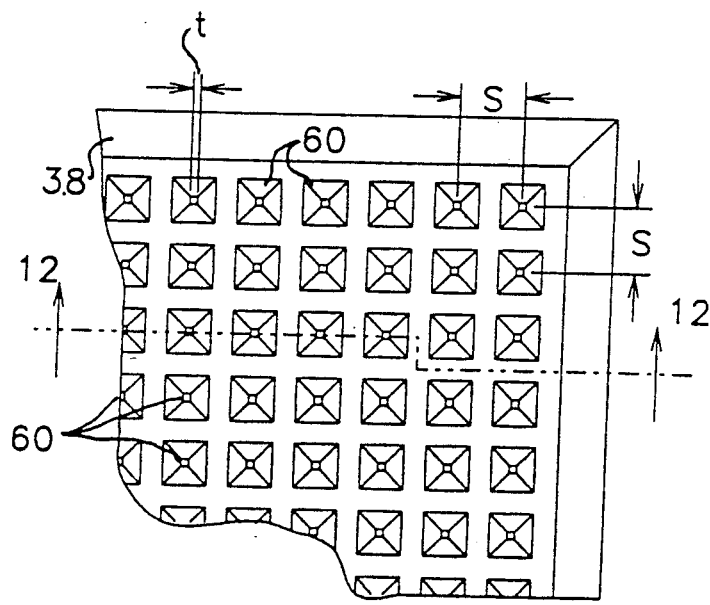
FIG. 11 is an enlarged fragmentary plan view of the area represented by the sight circle 10 in FIG. 2.
Figure 12:
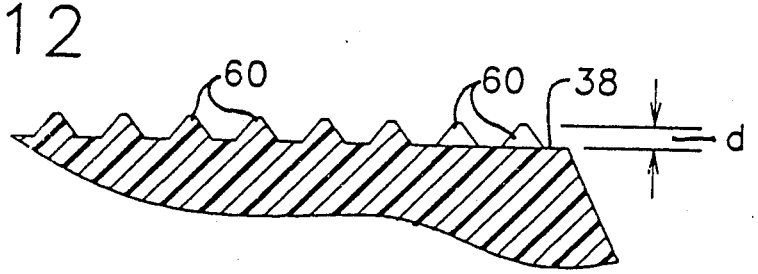
FIG. 12 is a fragmentary cross section on line 12—12 of FIG. 11.

The rectangular fluid transport surface 38, as described, projects from the interior of the well floor wall 36 to present a well defined rectangular planar surface at the open side of the first member 10. The surface 38 operates to assure the spread of a liquid between it and a parallel opposed surface as described in the above-mentioned copending U.S. patent application Ser. No. 210,732. To this end, and as shown in FIGS. 11 and 12 of the drawings, the planar surface 38 is relieved by a uniform pattern of projections 60. The fluid transport surface including the projections, together with the surface of the assay element which is retained in contact or virtual contact with the projections, defines a fluid flow zone wherein the surface 38 and the surface of the assay element are spaced apart a capillary distance to permit capillary flow of fluid between them. The height of the projections is generally from about 50 to about 150 microns and preferably from about 80 to about 120 microns. The illustrations of FIGS. 11 and 12 are greatly enlarged relative to the already enlarged illustration of FIGS. 1-4, for example, to provide an appreciation of the configuration and dimensioning of the projections 60. In particular, it will be noted that in a preferred embodiment of the present invention, the projections 60 are shaped as truncated rectangular pyramids which terminate at their outer ends in a square surface, the side dimensions of which are designated by the letter "t". In practice the, preferred size of the dimension t is approximately 0.05 millimeter. The surfaces of the projections diverge from their outer end toward the plane of the rectangular surface 38 at an angle of approximately 45° and are of a height "d" equal to approximately 0.10 millimeter. The pyramidal projections 60 are spaced on centers "S" both in rows extending parallel to the length of the shelf 38 and in columns extending across the width of the surface 38. The preferred size of the spacing dimension S is 0.38 millimeter.

As may be seen in FIGS. 1 and 2, the interior corners at the juncture of the end wall 22 with the side walls 16 and 18 are filled by bosses 62 and 64 which extend to flat end surfaces 66 and 68, respectively, spaced slightly inward of the peripheral lip 26 circumscribing the open side of the first member 10. A spacer pin 70 is located centrally of the surface 68 and projects slightly therefrom in a manner to establish the assembled position of the second member 14 in a manner to be described. Identical pin-like projections 70 are provided on each of the shelf-like formations 48 and 50 as well as on a bridge 72 extending from the inner wall surface of the cylindrical well 52 to the end wall 20.

Structural details of the second member 14 may be understood and appreciated by reference to FIGS. 1 and 5-8 of the drawings. As shown, the second member 14 is generally of plate-like configuration and of a peripheral contour to complement the open side of the first member 10 as defined by the inner chamfered surface 28 on the peripheral lip 26. The inner side of the bottom member is shown most completely in FIG. 1 to include a planar inner surface 74. A pair of locating lugs 76 project from the surface 74 at opposite ends of the member 14. As may be seen in the drawings, the lugs 76 taper so as to converge from the surface 74 to a truncated flat 78 defining the inner ends of each lug. A chamfer 80 joins the outer end surfaces of each lug 76 with the respective truncated flats 78 thereof. A central working portion of the bottom member 14 and particularly of the inner planar surface 74 thereof is defined longitudinally between three through-holes 82 located to fit over and receive the posts 42 projecting from the inner surface of the well floor wall 36 of the top member 10. Also a relatively large square read aperture 84 opens through the planar surface 74 and is offset slightly from the longitudinal center of the member 14.

The inner surface of the bottom member 14 is recessed along opposite sides of the central working area to establish a pair of parallel and generally elongated ramp surfaces 86 and 87 which diverge from the planar surface 74 at an angle a (see FIG. 8) and end at step-like planes 88 and 89, respectively. The ramp surfaces 86 and 87 on the bottom member 14 complement the ramp surfaces 44 and 46 in the top member 10. In this respect, the angle of inclination a is the same for both the ramps 86, 87 and the ramps 44, 46. A preferred angle a for the inclination of the surfaces from the plane of the rectangular fluid transport surface 38 in the top member 10 and from the plane of the surface 74 on the bottom member 14 is preferably on the order of 15°. As will be appreciated from the description to follow concerning the function of these ramps, the specific angle at which they are inclined may vary substantially from 15°.

Figure 5:
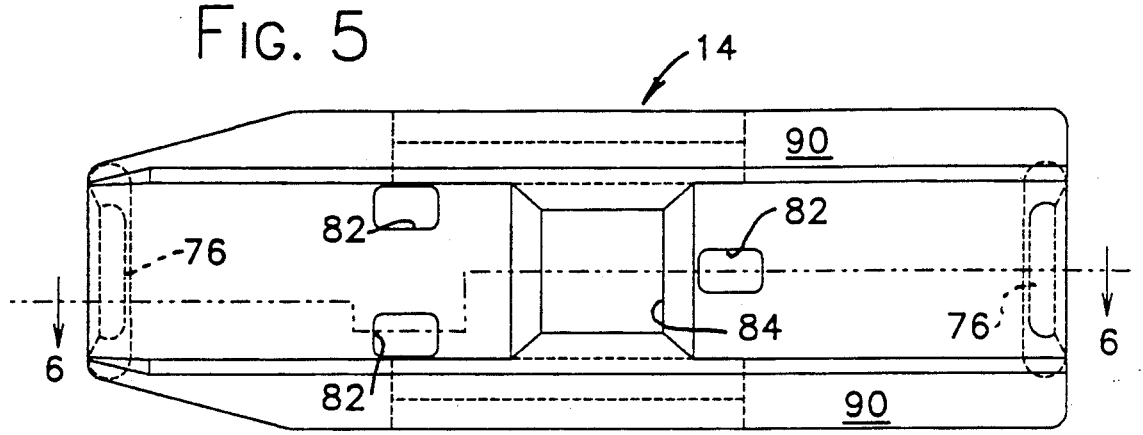
FIG. 5 is a bottom plan view of the other the two major components shown in FIG. 1 of the drawings.
Figure 6:
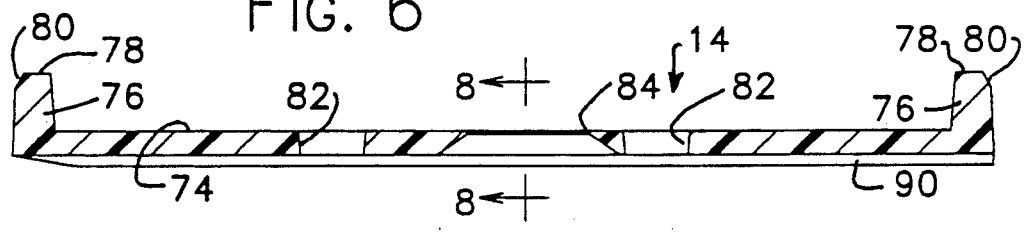
FIG. 6 is a section on line 6—6 of FIG. 5.
Figure 7:
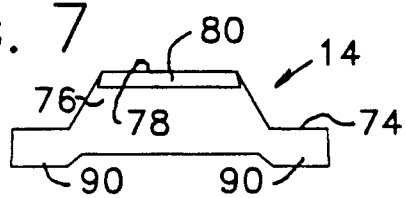
FIG. 7 is an end elevation of the part shown in FIGS. 5 and 6.
Figure 8:
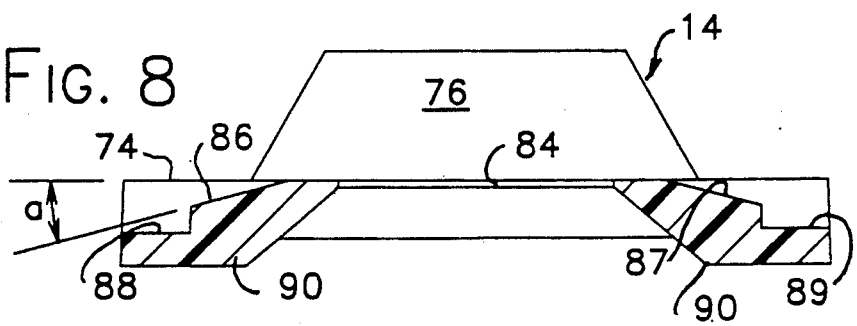
FIG. 8 is an enlarged cross section on line 8—8 of FIG. 6.

The outer surface of the bottom member 14 may be appreciated from FIGS. 5, 7 and 8 of the drawings. As shown particularly in FIGS. 5 and 8, the read opening 84 which opens through the inner planar surface 74, is delimited by a very narrow lip as a result of flaring the periphery of the opening toward the outer surface of the bottom member 14. A continuation of the outwardly flared opening 84 results in a pair of longitudinal rails 90 extending over the length of the member 14. The rails function not only to strengthen the bottom member 14 but also to allow an adequate amount of material to define the recesses on which the ramps 86, 87 and steps 88, 89 are located.

Figure 9:
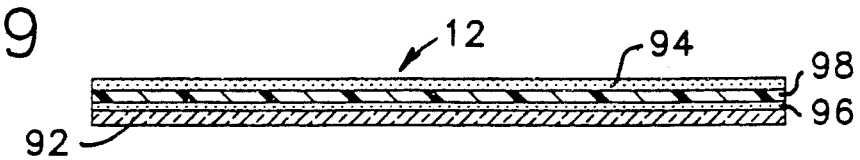
FIG. 9 is an enlarged cross section illustrating representative layers of a preferred embodiment of an assay element which may be incorporated in the assay module of the invention.

The assay element 12 may comprise any analytical assay element. Further, the assay element may be a single layer or a multilayer element. Assay elements which are based on immunological interactions are preferred. A typical thin film assay element has a thickness of about 0.1 mm and comprises one or more reagent layers residing on a support layer which is transparent to permit reading of the element from below. The assay element may also include various other layers such as are known in the art including, for example, a light-blocking layer to permit the signal generating species in one layer to be read out without interference from material present in another layer, a registration layer for holding a signal generating species formed in, or released from, another layer, etc. For the purpose of further illustrating the invention a particularly preferred multilayer assay element 12 is shown in FIG. 9. Specifically, one surface of the assay element 12 is defined by the outer surface of a transparent support layer 92 whereas the other surface of the assay element is defined by the outer surface of a layer 94 which may be a reagent layer, a protein filter layer, an anti-abrasion layer or the like. A reagent layer 96 and a light blocking layer 98 lie between the outer layers 92 and 94. Although the chemical and/or immunological properties of the assay element 12 in the use of the present invention for analytical procedures is important, the physical properties of the element are of greater significance to an understanding of the present invention. In particular, the sheet-like assay element 12 is not only very thin, as indicated, but because the support layer 92 is typically a polymeric material, it is resilient in the sense that if it is distorted out of its initial planar condition, it will exhibit a bias to its original position. Also the assay element is of generally rectangular configuration as shown in FIG. 1, and is of a size to extend onto and lie against the ramps 44 and 46 in the first member 10 as well as to lie between the posts 42 on opposite ends of the rectangular fluid transport surface 38.

In a particularly preferred embodiment reagent layer 96 comprises an immunocomplex of a fluorescent labeled antigen and an antibody directed against the antigen. In this embodiment the antibody is immobilized in reagent layer 96 such as by being covalently bound to the surface of support layer 92 or to a matrix material or by being physically held by the matrix material. In practice a sample fluid is introduced through the opening 40 in the first member 10 and is spread uniformly across the surface of the assay element 12 corresponding to the fluid flow zone defined by rectangular fluid transport surface 38. A substantially uniform concentration of any analyte present in the sample fluid is distributed across the assay element and the fluid diffuses throughout layers 94, 96 and 98 as well as filling the fluid flow zone between the surface of layer 94 of the assay element and the rectangular fluid transport surface 38 of first member 10. An equilibrium is established. When present, the sample analyte, in this illustrative discussion an antigen of interest, will compete with the fluorescent-labeled antigen (the same antigen as the sample antigen or an analogue thereof) for the available binding sites on the immobilized antibody. The fluorescent-labeled antigen initially complexed to the antibody in reagent layer 96 will be dissociated therefrom and replaced by the sample antigen in a ratio approximately equal to the relative amounts of sample antigen and fluorescent-labeled antigen. Thus, depending upon the amount of antigen present in the sample fluid, some percentage of the fluorescent-labeled antigen will bind to those immobilized antibodies which are not bound to the sample antigen. The remainder of the labeled antigen will be distributed throughout the remainder of the assay element, i.e., throughout layer 94 and 98, and the fluid flow zone between the surface of layer 94 and the opposed rectangular fluid transport surface 38 of the first member 10. The amount of labeled antigen bound to the immobilized antibodies in reagent layer 96 at any time is inversely proportional to the amount of sample antigen. A quantitative determination is obtained by irradiating the reagent layer 96 through the aperture 84 of the bottom member 14 with appropriate excitation energy. Since the reagent layer 96 which includes the immobilized antibody is preferably very thin in comparison to the combined thickness of layers 94 and 98 and the fluid flow zone, preferably a ratio of from about 1:20 to about 1:100 or more, and because light-blocking layer 98 prevents any of the excitation energy from entering layer 94 or the fluid flow zone, the optical readout system will measure the amount of labeled antigen which is bound to the immobilized antibody and a very small percentage of the free labeled antigen which is distributed throughout the remainder of the assay element and the fluid flow zone.

It will be appreciated by those skilled in the art that in this preferred embodiment it is very important to control the volume of fluid in the fluid flow zone. This is accomplished according to the invention by retaining the surface of the assay element in contact or in virtual contact with the projections 60 carried on fluid transport surface 38 by means of the flexure developed between the complementary ramp surfaces of the respective first and second members of the assay module.

Assembly of the first member 10, assay element 12 and the second member 14 is effected simply by placing the assay element 12 into the first member 10 so that the layer 94 faces the rectangular surface 38. This placement is facilitated by a combination of the three posts 42 and the formations 48 and 50 which serve to guide the element to a preliminary position in which the side edges of the element 12 rest on the ramps 44 and 46 and so that the top face of the element, that is, the outer surface of the layer 94, properly overlies the rectangular surface 38 to space the top surface initially from the surface 38. The second member 14 is then advanced into the open side of the first member 10 as depicted by phantom line illustration in FIG. 10 and also by the exploded perspective illustration in FIG. 1 of the drawings. Final guiding of the second member into position is aided by the tapered lugs 76 as well as by the continuous internal chamfer 28 on the peripheral lip 26 of the first member 10.

During final movement of the bottom member 14 into the top member 10, a combination of the ramps 86, 87 on the bottom member and the complementing inclination of the ramps 44, 46 in the top member result in a flexure of the assay element 12 so that the layer 94 in the illustrated embodiment of the assay element, which represents the top surface of the assay element, is biased by the inherent resiliency of the assay element into uniform continuous contact or virtual contact with the projections 60 on rectangular surface 38. The final position of the second member 14 is established by engagement of inner surfaces thereon with the projecting locator pins 70 spaced about the inner periphery of the first member 10. Once in place, the bottom member 14 is secured by appropriate means such as adhesives, ultrasonic fusion, or the like.

Figure 10:
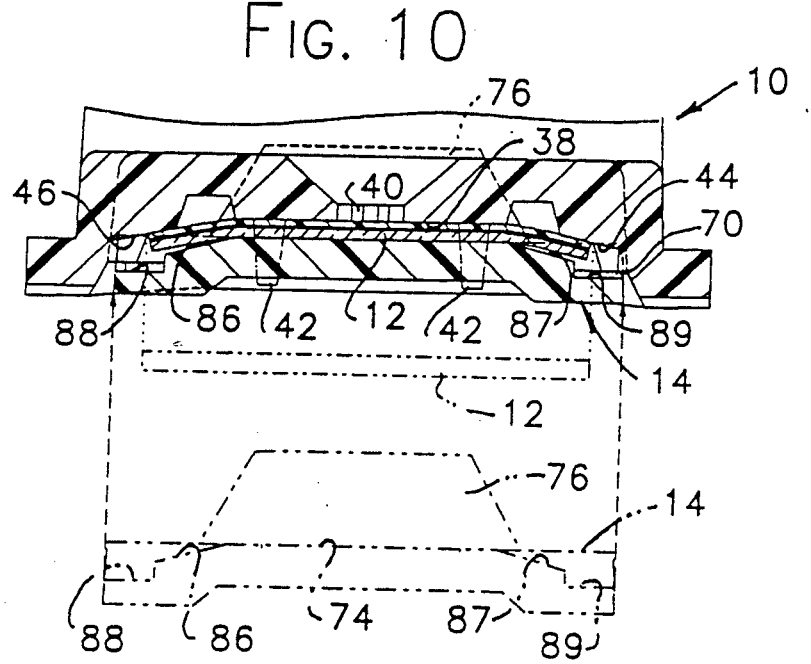
FIG. 10 is an enlarged cross section in the plane of FIG. 4 but with the components of the invention assembled.

The relationship of the three parts 10, 12 ..d 14 after assembly is shown most clearly in FIG. 10 of the drawings. In particular, it will be noted that the surface of the assay element 12 is constrained to be in contact or virtual contact with the truncated ends of the individual pyramid projections 60 on rectangular surface 38. This orientation of the assay element surface is, moreover, assured by flexure of the assay element 12 as a result of coaction between the respective ramps 44, 46 in the first member 10 and the ramps 86, 87 on the bottom member 14.

It is to be noted that the optical read opening 84 in the secondary member 14 is displaced so that it does not overlie any portion of the fill opening 40 in the first member 10. Because the size of the read opening 84, a substantial portion of the assay element 12 is unsupported by structure over a relatively large area of the fluid flow zone defined by rectangular surface 38. As noted above, the area of assay element 12 left out of contact by structure in the area of the opening 84 must lie in a planar configuration to be retained in contact or virtual contact with projections 60 on rectangular surface 38 for the purpose of controlling the volume of fluid in the fluid flow zone between the outer surface of layer 94 and rectangular surface 38 and for optical precision. Because of the manner in which the assay element is stressed to conform with the planar orientation of rectangular surface 38 in accordance with the invention this condition is assured.

Figure 13:
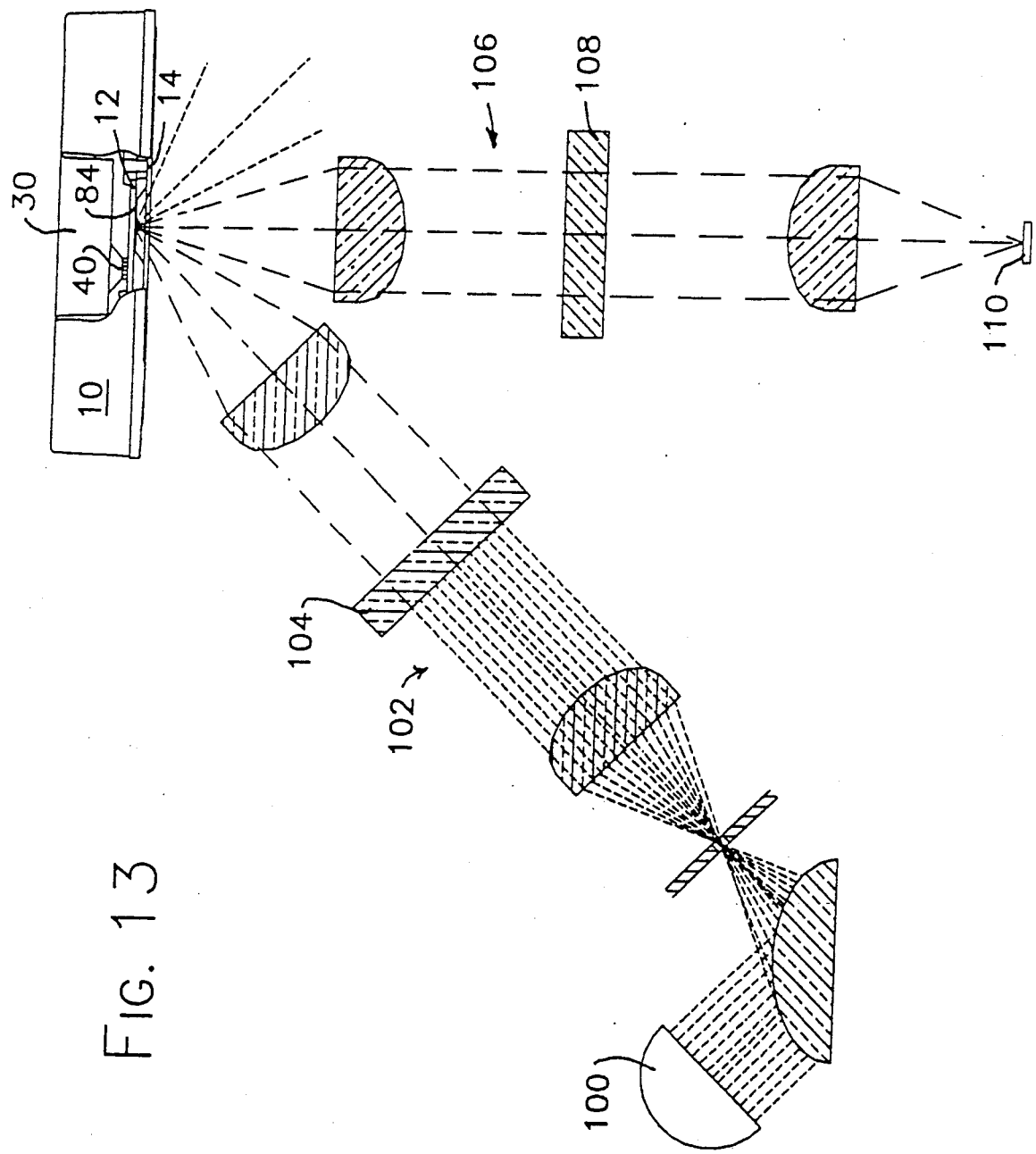
FIG. 13 is a generally schematic view illustrating the invention in relation to an optical read system.

In FIG. 13, the assembled assay module including the first member 10, the assay element 12 and the second member 14 are shown positioned relative to an optical system of the type disclosed in the above-mentioned commonly assigned copending application Ser. No. 378,647, now U.S. Pat. No. 4,977,325. In light of the detailed disclosure of the optical system in this copending application the components thereof need only be summarized in this instance as including a light source 100 from which broad band illumination is collimated along one channel 102 including a filter 104 to impinge against the transport support layer surface of the assay element 12, light energy of a specific narrow frequency range. Light emanating from the assay element 12 as a result of the interaction between a sample analyte and the reagent layers in the assay element is directed through a second separate channel 106 including a filter 108 to pass light of another specific wavelength to a sensor 110 to develop a voltage signal corresponding to the amount of analyte in the sample. As pointed out in the aforementioned copending application, the efficiency of the optical system is important particularly from the standpoint of being able to use a relatively inexpensive tungsten halogen lamp for the illumination source 100 and a photodetector for the sensor 110. Thus, not only is the planar orientation of the assay element 12 critical to efficiency of the optical reading system shown, but also the absence of any media underlying the bottom surface of the element 12 due to the read opening 84 in the second member 14 is important to optical efficiency of the system.

Thus, it will be appreciated that as a result of the present invention, a highly effective assay module is provided by which the stated objectives, among others, are completely fulfilled. Also, it will be understood by those skilled in the art from the preceding description and accompanying drawings that variations may be made in the disclosed preferred embodiments without departure from the invention. It is expressly intended, therefore, that the description and illustration is of preferred embodiments only, not limiting, and that the true spirit and scope of the present invention will be determined by reference to the appended claims.

What is claimed is:

1. A diagnostic assay module for analytical diagnostic procedures in which an optical signal developed by interaction between a component in a sample fluid and one or more reagents in a resilient assay element is read by optical means, said assay module comprising:
    a first member including wall means to define side walls, end walls and a top wall wherein the bottom of the first member is open, said first member further including inner and outer surface formations, said wall means including an opening to permit sample fluid to be introduced therethrough so as to be delivered to said assay element;
    a second member for closing said open bottom of said first member, said second member having an open optical read aperture positioned to be in registration with at least a substantial portion of said assay element when said assay element and said first and second members are assembled; and
    means for inclining opposite edges of said assay element at a downward angle to maintain the area of said assay element overlying said optical read aperture in a substantially planar configuration the assay element to maintain it in a controlled orientation.

2. The assay module as defined in claim 1 wherein said inner surface formations include a fluid transport surface presented toward said open bottom.

3. The assay module as defined in claim 2 wherein said fluid transport surface comprises a surface carrying a plurality of discrete noncontinuous projections spaced apart from each other in a predetermined pattern, said projections extending a capillary distance from said surface, and wherein a surface of said assay element is retained in contact or virtual contact with said projections.

4. The assay module as defined in claim 3 wherein said assay element edge inclining means comprises inner surface formations on said first member spaced on opposite sides of said fluid transport surface to engage the edges of the assay element, said inner surface formations being positioned closer to said open bottom of said first member than said fluid transport surface, is to said open bottom and means on said second member to complement said inner surface formations on said first member, in order to maintain said assay element in a convex configuration in relation to said fluid transport surface.

5. The assay module as defined in claim 4 wherein said inner surface formations comprise first ramp surfaces inclined downwardly toward said open bottom.

6. The assay module as defined in claim 5 wherein said means on said second member to incline the edges of the assay element comprises second ramp surfaces cooperable with said first ramp surfaces and having an inclination to complement said first ramp surfaces to constrain the side edges of the assay element to the inclination of said ramp surfaces.

7. The assay module as defined in claim 6 wherein said fluid transport surface is planar and wherein said ramp surfaces are inclined at an angle to said capillary surface of approximately 15°.

8. The assay module as defined in claim 3 wherein said projections are in truncated pyramidal form.

9. The assay module as defined in claim 2 wherein said sample fluid introducing opening extends between an outer surface formation of said first member and said fluid transport surface of said first member.

10. A diagnostic assay module for analytical procedures in which an optical signal developed by interaction between an analyte in a sample and one or more reagents in a resilient assay element is read by optical means, said assay module comprising:

an assay element;

a first member including mutually opposed side and end walls closed on one side by a covering wall and open at the side opposite from said covering wall, said first member having inner surface formations including a planar fluid transport surface carrying a plurality of discrete noncontinuous projections spaced apart from each other in a predetermined pattern, said projections extending a capillary distance from said transport surface and presented to face said open side of said first member;

a second member for closing said open side of said first member and having an unobstructed optical read aperture positioned to register with at least a substantial portion of said fluid transport surface when said first and second members are assembled; and cooperating ramp means on said first and second members for flexing the assay element into contact or virtual contact with said projections to retain said assay element in a planar configuration for optical reading by light passing through said read aperture.

11. The assay module as defined in claim 10 wherein said first member includes an exterior sample well on the side of said covering wall opposite from said fluid transport surface and a sample introducing aperture opening through said covering wall between the floor surface of said well and said fluid transport surface.

12. The assay module as defined in claim 11 wherein said first member further includes a pair of exterior fluid storing wells spaced from opposite ends of said sample well.

13. The assay module as defined claim 10 including guide means to facilitate assembly of said first and second members.

14. The assay module as defined in claim 13 wherein said guide means includes a continuous peripheral lip on the open side of said side and end walls, said lip having a chamfered surface along the inner edge thereof.

15. The assay module as defined in claim 14 wherein said guide means further includes a plurality of posts projecting from said covering wall toward said open side of said first member and a complementing plurality of apertures in said second member to receive said posts.

16. The assay module as defined in claim 15 wherein said guide means further includes a pair of tapered projections from the inner surface of said second member, said tapered projections being located at opposite ends of said second member.

17. The assay module as defined in claim 13 including a plurality of abutment pin formations projecting from the inner surface of said first member, said abutment pin formations establishing the assembled position of said second member relative to said first member.

* * * * *

UNITED STATES PATENT AND TRADEMARK OFFICE
CERTIFICATE OF CORRECTION

PATENT NO. : 5,053,197
DATED : October 1, 1991
INVENTOR(S) : M.S. Bowen

It is certified that error appears in the above-identified patent and that said Letters Patent is hereby corrected as shown below:

```
Column 3, line 62, after "other", insert
--- of ---.

Column 10,
Claim 1, lines 22-24, delete "the assay element
to maintain it in a controlled orientation".
```

Signed and Sealed this

Seventh Day of December, 1993

*Attest:*

BRUCE LEHMAN

*Attesting Officer*      *Commissioner of Patents and Trademarks*